United States Patent [19]

Schucker

[11] Patent Number: 5,221,481
[45] Date of Patent: * Jun. 22, 1993

[54] MULTI-BLOCK POLYMER COMPRISING AN ESTER PREPOLYMER, MADE BY COMBINING EPOXY WITH POLYESTER, CHAIN EXTENDED WITH A COMPATIBLE SECOND PREPOLYMER, THE MEMBRANE MADE THEREFROM AND ITS USE FOR SEPARATIONS

[75] Inventor: Robert C. Schucker, Baton Rouge, La.

[73] Assignee: Exxon Research and Engineering Company, Florham Park, N.J.

[*] Notice: The portion of the term of this patent subsequent to Sep. 17, 2008 has been disclaimed.

[21] Appl. No.: 624,426

[22] Filed: Dec. 6, 1990

[51] Int. Cl.$^5$ .............................................. B01D 61/36
[52] U.S. Cl. .............................. 210/640; 210/500.37
[58] Field of Search ............. 210/640, 500.37, 500.27, 210/500.28; 525/428, 113

[56] References Cited

U.S. PATENT DOCUMENTS

| | | | |
|---|---|---|---|
| 2,930,754 | 3/1960 | Stuckey | 210/23 |
| 2,958,656 | 11/1960 | Stuckey | 210/23 |
| 3,370,102 | 2/1968 | Carpenter et al. | 260/674 |
| 3,567,632 | 3/1971 | Richter et al. | 210/23 |
| 3,847,874 | 11/1974 | Murakami et al. | 260/77.5 |
| 3,993,630 | 11/1976 | Darmory et al. | 525/428 |
| 4,115,465 | 9/1978 | Elfert et al. | 260/674 |
| 4,298,707 | 11/1981 | Hergenrother et al. | 521/95 |
| 4,316,967 | 2/1982 | Hergenrother et al. | 525/111 |
| 4,386,191 | 5/1983 | DiSalvo et al. | 525/504 |
| 4,532,041 | 7/1985 | Shuey et al. | 210/500.2 |
| 4,690,873 | 9/1987 | Makino et al. | 428/473.5 |
| 4,746,474 | 5/1988 | Kohn | 264/41 |
| 4,839,203 | 6/1989 | Paus et al. | 210/500.27 X |
| 4,914,064 | 4/1990 | Schucker | 502/4 |
| 4,918,119 | 4/1990 | Seltmann et al. | 523/461 |
| 4,929,358 | 5/1990 | Koenitzer | 210/640 |
| 4,944,880 | 7/1990 | Ho et al. | 210/640 |
| 4,946,594 | 8/1990 | Thaler et al. | 210/651 |
| 4,990,275 | 2/1991 | Ho et al. | 252/62.3 |
| 5,049,281 | 9/1991 | Schucker | 210/654 X |

FOREIGN PATENT DOCUMENTS 255381 2/1988 European Pat. Off. .
361377 4/1990 European Pat. Off. .

Primary Examiner—Frank Spear
Attorney, Agent, or Firm—Joseph J. Allocca

[57] ABSTRACT

The present invention is directed to a multi-block polymeric material comprising an ester prepolymer chain extended with a second, different, compatible prepolymer selected from the group of prepolymers comprising (a) an (A) dianhydride or its corresponding tetraacid or diacid-diester combined with a monomer selected from (B) epoxy, diisocyanate, polyester, and diamine in an A/B mole ratio ranging from about 2.0 to 1.05, preferably about 2.0 to 1.1; and (b) an (A) diamine combined with a monomer selected from (B) epoxy, diisocyanate, and dianhydride or its corresponding tetraacid or diacid-diester in an A/B mole ratio ranging from about 2.0 to 1.05, preferably about 2.0 to 1.1, and mixtures thereof. The present invention is also directed to membranes of the above recited multi-block polymeric materials especially membranes comprising thin, dense films of said multi-block polymeric material deposited on a microporous support later producing a thin film composite membrane. The membranes of the multi-block polymeric material, especially the thin film composite membranes, are useful for separating aromatic hydrocarbons from mixtures of same with non-aromatic hydrocarbons under perstraction or pervaporation conditions.

14 Claims, No Drawings

MULTI-BLOCK POLYMER COMPRISING AN ESTER PREPOLYMER, MADE BY COMBINING EPOXY WITH POLYESTER, CHAIN EXTENDED WITH A COMPATIBLE SECOND PREPOLYMER, THE MEMBRANE MADE THEREFROM AND ITS USE FOR SEPARATIONS

DESCRIPTION OF THE INVENTION

The present invention is directed to a multi-block polymeric material comprising an ester prepolymer chain extended with a second, different, compatible prepolymer selected from the group of prepolymers comprising (a) an (A) dianhydride or its corresponding tetraacid or diacid-diester combined with a monomer selected from (B) epoxy, diisocyanate, polyester, and diamine in an A/B mole ratio ranging from about 2.0 to 1.05, preferably about 2.0 to 1.1; and (b) an (A) diamine combined with a monomer selected from (B) epoxy, diisocyanate, and dianhydride or its corresponding tetraacid or diacid-diester in an A/B mole ratio ranging from about 2.0 to 1.05, preferably about 2.0 to 1.1, and mixtures thereof.

The present invention is also directed to membranes of the above recited multi-block polymeric materials especially membranes comprising thin, dense films of said multi-block polymeric material deposited on a micro porous support layer producing a thin film composite membrane.

The membranes of the multi-block polymeric material, especially the thin film composite membranes, are useful for separating aromatic hydrocarbons including heteroatom containing aromatics from mixtures of same with non-aromatic hydrocarbons under perstraction or pervaporation conditions.

BACKGROUND OF THE INVENTION

Polyurea/urethane membranes and their use for the separation of aromatics from non-aromatics are the subject of U.S. Pat. No. 4,914,064. In that case the polyurea/urethane membrane is made from a polyurea/-urethane polymer characterized by possessing a urea index of at least about 20% but less than 100%, an aromatic carbon content of at least about 15 mole percent, a functional group density of at least about 10 per 1000 grams of polymer, and a C=O/NH ratio of less than about 8.0. The polyurea/urethane multi-block copolymer is produced by reacting di-hydroxy or polyhydroxy compounds, such as polyethers or polyesters having molecular weights in the range of about 500 to 5,000 with aliphatic, alkylaromatic or aromatic diisocyanates to produce a prepolymer which is then chain extended using diamines, polyamines or amino alcohols. The membranes are used to separate aromatics from non-aromatics under perstraction or pervaporation conditions.

The use of polyurethane imide membranes for aromatics from non-aromatics separations is disclosed in U.S. Pat. No. 4,929,358. The polyurethane imide membrane is made from a polyurethane-imide copolymer produced by end capping a polyol such as a dihydroxy or polyhydroxy compound (e.g. polyether or polyester) with a di or polyisocyanate to produce a prepolymer which is then chain extended by reaction of said prepolymer with a di or polyanhydride or with a di or polycarboxylic acid to produce a polyurethane amic acid which is then chemically or thermally cyclized to the imide. The aromatic/non-aromatic separation using said membrane is preferably conducted under perstraction or pervaporation conditions.

A polyester imide copolymer membrane and its use for the separation of aromatics from non-aromatics is the subject of U.S. Pat. No. 4,946,594. In that case the polyester imide is prepared by reacting polyester with a dianhydride to produce a prepolymer which is then chain extended with a diisocyanate to produce the polyester imide.

The use of membranes to separate aromatics from saturates has long been pursued by the scientific and industrial community and is the subject of numerous patents.

U.S. Pat. No. 3,370,102 describes a general process for separating a feed into a permeate stream and a retentate stream and utilizes a sweep liquid to remove the permeate from the face of the membrane to thereby maintain the concentration gradient driving force. The process can be used to separate a wide variety of mixtures including various petroleum fractions, naphthas, oils, hydrocarbon mixtures. Expressly recited is the separation of aromatics from kerosene.

U.S. Pat. No. 2,958,656 teaches the separation of hydrocarbons by type, i.e. aromatic, unsaturated, saturated, by permeating a portion of the mixture through a non-porous cellulose ether membrane and removing permeate from the permeate side of the membrane using a sweep gas or liquid. Feeds include hydrocarbon mixtures, naphtha (including virgin naphtha, naphtha from thermal or catalytic cracking, etc.).

U.S. Pat. No. 2,930,754 teaches a method for separating hydrocarbons e.g. aromatic and/or olefins from gasoline boiling range mixtures, by the selective permeation of the aromatic through certain cellulose ester non-porous membranes. The permeated hydrocarbons are continuously removed from the permeate zone using a sweep gas or liquid.

U.S. Pat. No. 4,115,465 teaches the use of polyurethane membranes to selectively separate aromatics from saturates via pervaporation.

DETAILED DESCRIPTION OF THE INVENTION

The present invention comprises a multi-block polymeric material comprising a first prepolymer, made by combining an (A) epoxy with (B) polyester, preferably an acid terminated polyester, in an A/B mole ratio ranging from about 2.0 to 1.05, preferably about 2.0 to 1.1 to produce an ester which is subsequently chain extended with a second compatible prepolymer selected from the group of prepolymers comprising (a) an (A) dianhydride or its corresponding tetraacid or diacid-diester combined with a monomer selected from (B) epoxy, diisocyanate, polyester, and diamine in an A/B mole ratio ranging from about 2.0 to 1.05, preferably about 2.0 to 1.1, and (b) an (A) diamine combined with a monomer selected from (B) epoxy, diisocyanate, and dianhydride or its corresponding tetraacid or diacid-diester in an A/B mole ratio ranging from about 2.0 to 1.05, preferably about 2.0 to 1.1, and mixtures thereof.

The present invention is also directed to membranes of the above recited multi-block polymeric materials, especially membranes comprising thin, dense (nonporous) films of said multi-block polymeric material deposited on a micro porous support layer producing a thin film composite membrane.

The membranes of the multi-block polymeric material, especially the thin film composite membranes are useful for separating aromatic hydrocarbons from mixtures of same with non-aromatic hydrocarbons under perstraction or pervaporation conditions. As used hereinafter in this text and the appended claims the term "aromatic hydrocarbons" is meant to include single and multi-ring side chain bearing and unsubstituted aromatics containing only carbon and hydrogen, single and multi-ring side chain bearing and unsubstituted heterocyclic aromatics such as thiophene, pyridine, quinoline benzothiophene, benzofuran, etc., and single and multi-ring aromatic and heterocyclic aromatics bearing heteroatom substituted side chains.

In preparing the multi-block polymeric material one begins by preparing a first prepolymer made by combining an (A) epoxy with a (B) polyester, preferably an acid terminated polyester, in an A/B mole ratio ranging from about 2.0 to 1.05, preferably about 2.0 to 1.1 to produce a prepolymer ether.

The epoxy used to produce the prepolymer ether is a di-epoxy of the general formula:

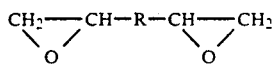

R may be any saturated, unsaturated, or aromatic group, halogen substituted saturated, unsaturated or aromatic group as well as groups containing oxygen in the form of ether linkages, and mixtures thereof.

Representative of useful epoxy compounds are the following:

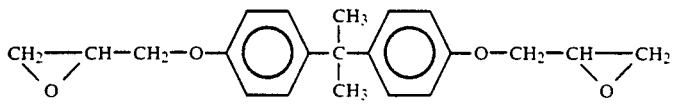

identified as DER332 from Dow Chemical and

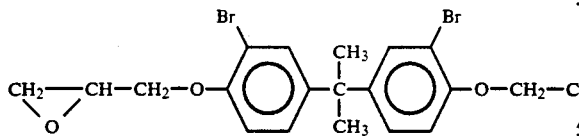

identified as DER542 from Dow Chemical

Polyesters, preferably acid terminated polyesters, having molecular weights in the range of about 500 to 5000 are used in preparing the prepolymer ether.

The polyester components are prepared from aliphatic or aromatic dicarboxylic acids and aliphatic or aromatic dialcohols. Aliphatic dicarboxylic acids refer to those materials having the general formula HOOCRCOOH where R contains 2 to 10 carbons (and may be either a straight or branched chain configuration). Aromatic dicarboxylic acids refer to those materials having the general structure HOOCRCOOH where R is:

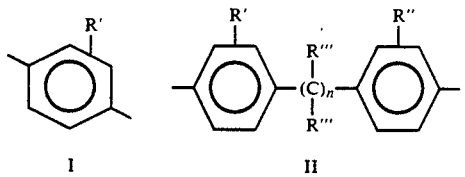

wherein R', R", and R''', may be the same or different and are selected from the group consisting of H and $C_1$-$C_5$ carbons or $C_6H_5$ and combinations thereof, and n is 0 to 4. It is to be understood that in the above formula each R' or R" may itself represent a mixture of H, $C_1$-$C_5$ or $C_6H_5$.

Dialcohols have the general structure HOROH where R may be

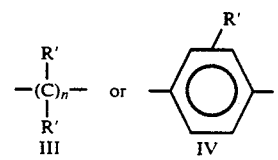

where n is 1 to 10, preferably 4 to 6, and R' is H, $C_1$ to $C_5$ or $C_6H_5$ or

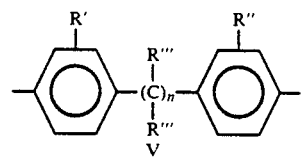

where R', R", R''' and n are defined in the same manner as for the aromatic dicarboxylic acids. An example of a useful dialcohol is bisphenol A.

The (A) epoxy and (B) polyester are combined in an A/B mole ratio ranging from about 2.0 to 1.05, preferably about 2.0 to 1.1. The reaction between these two reactants is run to completion. Completion of the reaction can be determined by any technique known to those skilled in the art to monitor the reaction of epoxy and polyester. For example, completion can be monitored by following the disappearance of epoxy groups. A doubling of the grams of prepolymer per equivalent of epoxy would evidence completion of the reaction.

The reaction can be run neat, i.e. in the absence of any added solvent. Alternatively the reaction can be run in the presence of an added polar, aprotic solvent such as dimethylformamide (DMF), N-methyl pyrrolidone (NMP), dimethyl acetamide (DMAc), dimethyl sulfoxide (DMSO) etc.

The second compatible prepolymer which is added to the ester prepolymer is selected from the group of prepolymers comprising (a) an (A) dianhydride or its corresponding tetraacid or diacid-diester combined with a monomer selected from (B) epoxy, diisocyanate, polyester, and diamine in an A/B mole ratio ranging from about 2.0 to 1.05, preferably about 2.0 to 1.1, and (b) an (A) diamine combined with one mole of a monomer selected from (B) epoxy, diisocyanate, and dianhydride or its corresponding tetraacid or diacid-diester in an A/B mole ratio ranging from about 2.0 to 1.05, preferably about 2.0 to 1.1 and mixtures thereof.

The epoxy and polyester materials used in preparing these second prepolymers are selected from the same groups of epoxies and polyesters described previously for the production of the first prepolymer ether.

In preparing the second prepolymer, aliphatic and cycloaliphatic di and polyisocyanate can be used as can be mixtures of aliphatic, cycloaliphatic, aralkyl and aromatic polyisocyanates.

The diisocyanates are preferably aromatic diisocyanates having the general structure:

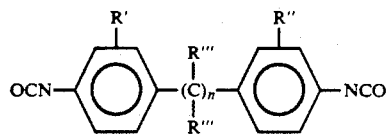

wherein R' and R" are the same or different and are selected from the group consisting of H, $C_1$–$C_5$ and $C_6H_5$ and mixtures thereof and n ranges from 0 to 4.

Aliphatic diisocyanates which may be utilized are exemplified by hexamethylene diisocyanate (HDI), 1,6-diisocyanato-2,2,4,4-tetramethylhexane (TMDI), 1,4-cyclohexanyl diisocyanate (CHDI), isophorone diisocyanate (IPDI), while useful alkylaromatic diisocyanates are exemplified by 2,4-toluene diisocyanate (TDI) and bitolylene diidocyanate (TODI). Aromatic diisocyanates are exemplified by 4,4'-diisocyanate diphenylmethane (MDI) methylene dichlorophenyl diisocyanate (dichloro MDI), methylene dicyclohexyl diisocyanate (H12-MDI), methylene bis [dichlorophenyl isocyanate] (tetrachloro MDI), and methylene bis [dichlorocyclohexyl isocyanate](tetrachloro - $H_{12}$MDI). Polyisocyanates are exemplified by polymeric MDI (PMDI) and carbodiimide modified MDI and isocyanurate isocyanates.

Diamines which can be used have the general formula $H_2NRNH_2$ where R includes aliphatic and aromatic moieties, such as

where n is 1 to 10 and R' may be the same or different and are selected from the group consisting of H, $C_1$–$C_5$ carbons and $C_6H_5$ and mixtures thereof.

Also included are diamines of the formula:

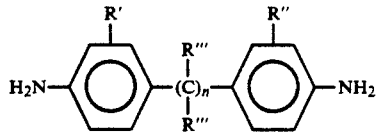

where R', R" and R'" are the same or different and are selected from the group consisting of H or Cl or a $C_1$ to $C_5$ or $C_6H_5$ and mixtures thereof and n ranges from 0 to 4.

Useful polyamines are exemplified by polyethyleneimines and 2,2',2'" triaminotriethylamine. Useful amino alcohols are exemplified by 6-aminohexanol, 4-aminophenol, 4-amino-4,-hydroxyl-diphenylmethane.

Dianhydrides or tetracarboxylic acids or diacid-diesters which produce amide acid groups are also used in producing the second prepolymer.

Any aromatic, aliphatic, cycloaliphatic or araliphatic dianhydride can be used. Examples of dianhydrides include by way of example and not limitation: pyromellitic dianhydride, 3,3',4,4'-benzophenone tetracarboxylic dianhydride, 4,4'-(hexafluoroisopropylidene)-bis-(phthalic anhydride), 4,4'-oxydiphthalic anhydride, diphenylsulfone-3,3'4,4'-tetracarboxylic dianhydride, and 3,3',4,4'-biphenyltetracarboxylic dianhydride.

Dicarboxylic acid/diester and tetracarboxylic acid derivatives of dianhydrides when used must first be converted to species that will react with diamines or polyesters. This can be done by conversion of the dicarboxylic acid/diester or tetracarboxylic moieties to (1) acid chlorides via derivatization with e.g. thionyl chloride or to (2) diimidazoles via reaction with e.g. carbonyl diimidazole. Subsequent reaction of the derivatized prepolymer with (1) diamines results in formation of an amide acid which must then be thermally or chemically cyclized to form the imide, or (2) polyesters results in formation of an ester which requires no further curing.

In each instance the appropriate monomeric materials in the aforementioned mole ratios are combined to produce the desired second prepolymer. Depending on the physical nature of the second prepolymer the reagents are combined and either reacted to completion or to a point short of completion. The reaction is run to completion when such second prepolymer exists in liquid or solution in solvent form. If however the second prepolymer when run to completion is in the form of a solid or insoluble gel then reaction to completion is unacceptable. In such instances the reagents are reacted until just before the viscosity of the reaction mixture becomes too difficult to manage. The second prepolymer is then, combined with the first prepolymer.

The first and second prepolymers can be reacted neat, i.e., in the absence of added solvent, if their individual natures favor such absence of solvent, or the reaction can be run in the presence of a solvent appropriate for the polymerization conditions employed. In general the reaction will be run in a solvent which may be selected from any of the polar, aprotic solvents such as tetrahydrofuran (THF), DMAc, DMSO, DMF, as well as NMP and cellosolve acetate.

Certain combinations of first prepolymer and second prepolymer may be reacted to completion while other combinations must be used to cast a membrane before the reaction goes to completion, i.e. while the reactant solution is still of a manageable viscosity and before formation of a gel. In those instances, which can be determined by the practitioner using the information before him in this specification without the expenditure of any inventive effort, the solution is spread or poured on the appropriate support, the copolymer layer on support inserted into an oven to drive off the casting solution solvent then heated to a temperature for a time sufficient to drive the polymerization reaction to completion and cure the membrane.

The multi-block polymer in solvent or dissolved in an added solvent is used as a casting solution. Polymer concentration in solvent ranges from 10 to 70 wt % preferably 15–50 wt % for casting dense films. When casting integral thin film composite membranes, e.g.

thin layers of polymer preferably about 0.1 to 5.0 microns thick on microporous support backings such as ceramic, sintered glass or metal or polymeric material such as nylon, porous polypropylene, porous teflon, or porous urea, preferably porous teflon, the polymer concentration in solution is on the order of about 50% or less.

The casting solution is poured or spread on an appropriate support medium, such as a metal or glass plate or, if desired, a woven fiber backing, such as woven fiber glass, nylon, polyester, etc. can be used if solvent removal during the casting sequence employs a vacuum, but preferably, non-woven backings such as thin films of porous polypropylene, porous urea or porous Teflon® are employed In general, however, backing materials used are those which are not attacked by the solvent(s) used to produce the copolymer casting solution and which can survive in the environment (chemical and thermal) to which the membrane will be exposed.

The membrane may be cast in any thickness, membranes ranging in thickness of from about 0.1 to about 50 microns being preferred, the thin, dense layer in the composite membrane being preferably about 0.1 to 5.0 microns thick.

A very thin layer of the multi-block polymer can be deposited onto a highly permeable, non-selective under layer producing a composite membrane comprising a thin, dense layer of multi-block polymer membrane about 0.1 to 5 microns thick on a permeable, non-selective, thick backing. The thick underlayer (about 20 to 100 microns thick) serves as a support layer permitting one to produce thin, dense, selective layers of multi-block polymer membranes which would otherwise be mechanically unmanageable due to their thinness. In many instances due to the chemical similarity between the support layer and the selective layer, the two layers interact through hydrogen bonding to produce a very strong bond in addition to physical adhesion. For general low temperature applications the porous, non-selective backing need not itself be capable of operating at high temperatures. In such service, such as the perstractive separation of aromatics from non-aromatics, backings such as polyurethane or polyurea/urethane would be sufficient. For high temperature applications, of course, the backing material must itself be capable of remaining intact at the high temperature. For such applications backing such as polyrester/imide, Teflon®, or even ceramics, sintered glass or metal supports should be used.

If one were to use this technique to produce sheet material, the thick, permeable underlayer such as polyurethane can be deposited on a suitable casting backing material such as glass, metal, porous fiber glass, polyethylene, polypropylene, nylon, Teflon®, etc. after which the thin, dense selective layer would be deposited onto the underlayer. The casting backing material can then be removed leaving the composite sheet membrane.

In producing hollow fibers or tubes using this composite membrane technique, first a tube or hollow fiber of permeable material such as nylon, polyurea, teflon or polyurethane is produced after which a thin dense layer of the multi-block polymer material is deposited on either the outer or inner surface of the tube or fiber support.

The permeable polyurethane layer can be prepared from polyether glycols such as polypropylene glycol or polybutylene glycol plus aliphatic and/or aromatic diisocyanates (preferably aliphatic diisocyanates) using polyols (diols or triols) preferably aliphatic diols as chain extenders. Polyurethane membrane materials which satisfy the above requirement of permeability are the polyurethane membranes described in U.S. Pat. No. 4,115,465.

The membranes are useful for the separation of aromatics from non-aromatics in petroleum and chemical streams, and have been found to be particularly useful for the separation of larger, substituted aromatics from non-aromatics as are encountered in heavy cat naphtha streams. Other streams which are also suitable feed streams for aromatics from saturates separation are intermediate cat naphtha streams (200°-320° F.), light aromatics content streams boiling in the $C_5$-300° F. range, light catalytic cycle oil boiling in the 400°-650° F. range, reformate streams as well as streams in chemical plants which contain recoverable quantities of benzene, toluene, xylene (BTX) or other aromatics in combination with saturates. The separation techniques which may successfully employ the membranes of the present invention include perstraction and pervaporation.

Perstraction involves the selective dissolution of particular components contained in a mixture into the membrane, the diffusion of those components through the membrane and the removal of the diffused components from the downstream side of the membrane by use of a liquid sweep stream. In the perstractive separation of aromatics from saturates in petroleum or chemical streams (particularly heavy cat naphtha streams) the aromatic molecules present in the feedstream dissolve into the membrane film due to similarities between the membrane solubility parameter and those of the aromatic species in the feed. The aromatics then permeate (diffuse) through the membrane and are swept away by a sweep liquid which is low in aromatics content. This keeps the concentration of aromatics at the permeate side of the membrane film low and maintains the concentration gradient which is responsible for the permeation of the aromatics through the membrane.

The sweep liquid is low in aromatics content so as not to itself decrease the concentration gradient. The sweep liquid is preferably a saturated hydrocarbon liquid with a boiling point much lower or much higher than that of the permeated aromatics. This is to facilitate separation, as by simple distillation. Suitable sweep liquids, therefore, would include, for example, $C_3$ to $C_6$ saturated hydrocarbons and lube basestocks ($C_{15}$-$C_{20}$).

The perstraction process is run at any convenient temperature, preferably as low as possible.

The choice of pressure is not critical since the perstraction process is not dependent on pressure, but on the ability of the aromatic components in the feed to dissolve into and migrate through the membrane under a concentration driving force. Consequently, any convenient pressure may be employed, the lower the better to avoid undesirable compaction, if the membrane is supported on a porous backing, or rupture of the membrane, if it is not.

If $C_3$ or $C_4$ sweep liquids are used at 25° C. or above in liquid state, the pressure must be increased to keep them in the liquid phase.

Pervaporation, by comparison, is run at generally higher temperatures than perstraction with the feed being in either liquid or vapor form and relies on vacuum or a sweep gas on the permeate side to evaporate or otherwise remove the permeate from the surface of the membrane and maintain the concentration gradient driving force which drives the separation process. As in perstraction, the aromatic molecules present in the feed dissolve into the membrane film, migrate through said film and reemerge on the permeate side under the influence of a concentration gradient Pervaporation separation of aromatics from saturates can be performed at a temperature of about 25° C. for the separation of benzene from hexane but for separation of heavier aromatic/saturate mixtures, such as heavy cat naphtha, higher temperatures of at least 80° C. and higher, preferably at least 100° C. and higher, more preferably 120° C. and higher (up to about 170° to 200° C. and higher) can be used, the maximum upper limit being that temperature at which the membrane is physically damaged. Vacuum on the order of 1-50 mm Hg is pulled on the permeate side. The vacuum stream containing the permeate is cooled to condense out the highly aromatic permeate. Condensation temperature should be below the dew point of the permeate at a given vacuum level.

The membrane itself may be in any convenient form utilizing any convenient module design. Thus, sheets of membrane material may be used in spiral wound or plate and frame permeation cell modules. Tubes and hollow fibers of membranes may be used in bundled configurations with either the feed or the sweep liquid (or vacuum) in the internal space of the tube or fiber, the other material obviously being on the other side.

Most conveniently, the membrane is used in a hollow fiber configuration with the feed introduced on the exterior side of the fiber, the sweep liquid flowing on the inside of the hollow fiber to sweep away the permeated highly aromatic species, thereby maintaining the desired concentration gradient. The sweep liquid, along with aromatics contained therein, is passed to separation means, typically distillation means, however, if a sweep liquid of low enough molecular weight is used, such as liquefied propane or butane, the sweep liquid can be permitted to simply evaporate, the liquid aromatics being recovered and the gaseous propane or butane (for example) being recovered and reliquefied by application of pressure or lowering the temperature.

The present invention will be better understood by reference to the following Examples which are offered by way of illustration and not limitation.

EXAMPLE 1

An epoxy-terminated ester prepolymer was made in the following way. Twenty grams (115 meq epoxy) of diglycidyl ether of Bisphenol A (DER332 from Dow) were mixed with 28.2 grams (57.5 meq) acid terminated polyethylene adipate (MW about 1000) at 100° C. to homogeneously mix. Twenty five grams of the mixture were removed to a separate flask to which were added 25.0 grams N-methyl pyrrolidone and 0.1 grams Dabco TMR-2 catalyst Initial epoxy content was 838 grams/equivalent. After 47 minutes, the epoxy level was 2134 grams/equivalent, indicating that somewhat more than half of the epoxy groups had reacted.

EXAMPLE 2

An amine-terminated epoxy prepolymer was made by dissolving 20.92 grams (102 meq NH2) 2,2-bis[4-(4-aminophenoxy)phenyl]propane.(BAPP) in 29.52 grams NMP. To this was added 8.67 grams (50 meq epoxy) diglycidyl ether of Bisphenol-A. The mixture was heated with stirring at 51° C. for 5 hours. The resulting solution had approximately 0.881 meq/gm $NH_2$.

EXAMPLE 3

To 5.00 grams (2.34 meq free epoxy) of prepolymer from Example 1 were added 2.66 grams (2.34 meq $NH_2$) of prepolymer from Example 2. The mixture was poured into a Teflon mold and placed into an oven at 148° C. under flowing nitrogen overnight. A membrane of approximately 378 microns thickness was cut out of the resulting film and tested for pervaporative separation of aromatics from saturates using a model feed containing 10 wt % toluene, 40 wt % p-xylene, 20 wt % isooctane and 30 wt % n-octane. A helium sweep gas at 100 cc/min was used to remove permeate from the downstream side of the membrane. Results of the test are shown in Table I for four temperatures evaluated.

TABLE I

| Temperature (°C.) | Selectivity | | Permeability (kg-μ/m²/d) |
|---|---|---|---|
| | Toluene/n-Octane | p-Xylene/n-Octane | |
| 90 | 8.29 | 5.70 | 248 |
| 100 | 7.84 | 5.53 | 451 |
| 110 | 7.16 | 5.10 | 764 |
| 120 | 6.79 | 4.86 | 1218 |

EXAMPLE 4

An anhydride-terminated prepolymer was made by dissolving 3.1 grams (20 meq anhydride) oxydiphthalic anhydride in 12.4 grams NMP. Separately, 0.87 gram (10 meq NCO) toluene diisocyanate was mixed with 3.48 grams NMP. The two solutions were mixed well and reacted with stirring at 100° C. for 2 hours until evolution of $CO_2$ gas ceased. The final solution had 0.504 meq free anhydride/gram solution.

EXAMPLE 5

To 2.00 grams (1.008 meq anhydride) of prepolymer from Example 4 were added 2.15 grams (1.008 meq epoxy) of prepolymer from Example 1. The solutions were mixed well, poured into a Teflon mold and placed into an oven at 148° C. under flowing nitrogen overnight. A film was cut from the resulting casting and tested for pervaporative separation of the same feed used in Example 3. Thickness of this membrane was 338 microns. Results of the testing are shown in Table II.

TABLE II

| Temperature (°C.) | Selectivity | | Permeability (kg-μ/m²/d) |
|---|---|---|---|
| | Toluene/n-Octane | p-Xylene/n-Octane | |
| 90 | 10.04 | 6.75 | 131 |
| 100 | 9.57 | 6.57 | 1235 |
| 110 | 9.37 | 6.59 | 384 |
| 120 | 7.79 | 6.16 | 614 |

EXAMPLE 7

An amine-capped prepolymer was formed by dissolving 8.21 grams (40 meq amine) BAPP in 32.87 grams NMP. Subsequently, 3.10 grams (20 meq anhydride) oxydiphthalic anhydride were dissolved in 12.40 grams NMP. The two solutions were mixed well and stirred overnight at room temperature to form a polyamic acid prepolymer end-capped with amine.

EXAMPLE 8

Approximately 2.5 grams (1.768 meq amine hydrogen) of prepolymer from Example 7 was mixed with 3.77 grams 1.768 meq epoxy of prepolymer from Example 1 and poured into a Teflon mold. The solution was dried in an oven under nitrogen flow overnight at 148° C. and produced a good film approximately 478 microns thick. Testing with the model feed from Example 3 under the same pervaporative conditions as shown in Example 3 (except that the helium sweep gas was 50 cc/min) produced the results shown in Table III.

TABLE III

| Temperature (°C.) | Selectivity | | Permeability (kg-μ/m²/d) |
|---|---|---|---|
| | Toluene/n-Octane | p-Xylene/n-Octane | |
| 90 | 8.22 | 5.6 | 101 |
| 100 | 7.61 | 5.31 | 172 |
| 110 | 7.23 | 5.58 | 291 |
| 120 | 6.81 | 4.88 | 420 |

As can be seen from these examples, all of these membranes are effective for the separation of aromatics from non-aromatics.

What is claimed is:

1. A method for separating aromatic hydrocarbons from feed streams comprising mixtures of aromatic hydrocarbons and non-aromatic hydrocarbons, said method comprising contacting the feed stream with one side of a membrane made from a multi-block polymer material comprising a first prepolymer made by combining an (A) epoxy with a (B) polyester in an A/B mole ratio ranging from about 2.0 to 1.05 to produce an ester which is subsequently chain extended with a second compatible prepolymer selected from the group consisting of (a) an (A) dianhydride or its corresponding tetraacid or diacid-diester combined with a monomer selected from the group consisting of (B) epoxy, diisocyanate, polyester and diamine in an A/B mole ratio ranging from about 2.0 to 1.05 and (b) an (A) diamine combined with a monomer selected from the group consisting of (B) epoxy, diisocyanate, and dianhydride or its corresponding tetraacid or diacid-diester in an A/B mole ratio ranging from about 2.0 to 1.05, and mixtures thereof, said separation being conducted under prevaporation or perstraction conditions, whereby the aromatic hydrocarbon components of the feed stream selectively permeate through the membrane.

2. The method of claim 1 wherein the polyester used to produce the first prepolymer is an acid terminated polyester.

3. The method of claim 1 or 2 wherein the membrane comprises a thin, dense film of said multiblock polymeric material deposited on a microporous support layer producing a thin film composite membrane.

4. The method of claim 3 wherein the microporous support layer is nylon, porous polypropylene, porous Teflon®, porous polyurethane or porous polyurea.

5. The method of claim 3 wherein the membrane layer ranges from about 0.1 to about 50 microns in thickness.

6. The method of claim 4 wherein the membrane layer ranges from about 0.1 to about 5.0 microns in thickness.

7. A membrane made of a multi-block polymer comprising a first prepolymer made by combining an (A) epoxy with a (B) polyester in an A/B mole ratio ranging from about 2.0 to 1.05 to produce an ether which is subsequently chain extended with a second compatible prepolymer selected from the group consisting of (a) an (A) dianhydride or its corresponding tetraacid or diacid-diester combined with a monomer selected from the group consisting of (B) epoxy, diisocyanate, polyester and diamine in an A/B mole ratio ranging from about 2.0 to 1.05, and (b) an (A) diamine combined with a monomer selected from the group consisting of (B) epoxy, diisocyanate, and dianhydride or its corresponding tetraacid or diacid-diester in an A/B mole ratio ranging from about 2.0 to 1.05, and mixtures thereof.

8. The membrane of claim 7 wherein the polyester used to produce the first prepolymer is an acid terminated polyester.

9. The membrane of claim 7 or 8 comprising a thin, dense film of said multi block polymer material deposited on a micro-porous support layer producing a thin film composite membrane.

10. The membrane of claim 9 wherein the microporous support layer is nylon, porous polypropylene, porous Teflon®, porous polyurea or porous polyurethane.

11. The membrane of claim 9 wherein the membrane layer ranges from about 0.1 to about 50 microns in thickness.

12. The membrane of claim 10 wherein the membrane layer ranges from about 0.1 to about 5.0 microns in thickness.

13. A multi-block polymer comprising a first prepolymer made by combining an (A) epoxy with a (B) polyester in an A/B mole ratio ranging from about 2.0 to 1.05 to produce an ester which is subsequently chain extended with a second compatible prepolymer selected from the group consisting of (a) an (A) dianhydride or its corresponding tetraacid or diacid-diester combined with a monomer selected from the group consisting of (B) epoxy, diisocyanate, polyester and diamine in an A/B mole ratio ranging from about 2.0 to 1.05, and (b) an (A) diamine combined with a monomer selected from the group consisting of (B) epoxy, diisocyanate, and dianhydride or its corresponding tetraacid or diacid-diester in an A/B mole ratio ranging from about 2.0 to 1.05, and mixtures thereof.

14. The multi-block polymer of claim 13 wherein the polyester used to produce the first prepolymer is an acid terminated polyester.

* * * * *